United States Patent [19]

Gvaryahu et al.

[11] Patent Number: 5,010,851

[45] Date of Patent: * Apr. 30, 1991

[54] METHODS OF RAISING COMMERCIAL ANIMALS

[75] Inventors: Gadi Gvaryahu, Rehovot, Israel; Danis L. Cunningham, Athens, Ga.

[73] Assignee: Cornell Research Foundation, Inc., Ithaca, N.Y.

[*] Notice: The portion of the term of this patent subsequent to Apr. 3, 2007 has been disclaimed.

[21] Appl. No.: 502,276

[22] Filed: Apr. 2, 1990

Related U.S. Application Data

[63] Continuation-in-part of Ser. No. 58,116, Jun. 4, 1987, Pat. No. 4,913,092, and a continuation-in-part of Ser. No. 217,977, Jul. 12, 1988.

[51] Int. Cl.$^5$ .............................................. A01K 31/00
[52] U.S. Cl. ........................................ 119/174; 119/29
[58] Field of Search .............................. 119/1, 29, 174

[56] References Cited

U.S. PATENT DOCUMENTS 4,913,092  4/1990  Gvaryahu ........................... 119/174

*Primary Examiner*—Paul J. Hirsch
*Attorney, Agent, or Firm*—Jones, Tullar & Cooper

[57] ABSTRACT

Methods for raising commercial farm animals including birds, fish and mammals, are disclosed which improve the animals' behavioral characteristics, feeding habits and mortality rates. In one embodiment of the invention, precocial birds are exposed to the combined effects of filial imprinting, environmental enrichment and music as they are raised. In another embodiment, various types of commercial farm animals are exposed to toys.

9 Claims, No Drawings

METHODS OF RAISING COMMERCIAL ANIMALS

CROSS REFERENCE TO RELATED APPLICATIONS

This application is a continuation-in-part of application Ser. No. 07/058,116, now U.S. Pat. No. 4,913,092 which was filed on June 4, 1987, and also is a continuation-in-part of application Ser. No. 07/217,977, which was filed on July 12, 1988.

BACKGROUND OF THE INVENTION

The present invention relates to methods for raising commercial or farm animals, such as birds, fish and mammals, which improve the animals' behavioral characteristics, feeding habits and mortality rates. More particularly, the invention to relates to a method of raising precocial birds utilizing filial imprinting, environmental enrichment and music, and a method of raising farm animals by exposing them to toys.

Filial imprinting, the attachment of young birds to the first object they encounter, is a widely studied phenomenon. The attachment of precocial birds to an imprinting object may be expressed as physical contact, approach response, orienting movements, or reduction of stress behavior. Experiments with 10 day old chicks have suggested that the use of an imprinting stimulus or commonal feeding may have an effect on weight gain in young chicks when compared to chicks fed in isolation. Recent experiments have shown that large populations of heavy strain chicks can be attached to an imprinting stimulus, and the imprinting objects can then be used to move birds from a training area to a new location. In addition to facilitating movement, imprinted chicks spatially distributed themselves more equally in a new area around the imprinting objects. In this initial study, the imprinting objects provided recorded bird sounds to enhance the imprintability of the chicks.

The present inventors have newly observed that imprinted chicks appeared to be less fearful than controls. In addition, imprinted chicks appeared to feed more frequently.

Environmental enrichment involves the increase of stimulus value of the home environment by increasing its complexity. There is considerable evidence that environmental enrichment results in marked behavioral and physiological effects on mammals. In contrast to the many mammalian studies, very little is known about the effect of environmental enrichment on birds. In one study, however, it was found that environmental enrichment improved body weight gain, relative body weight gain and gain:food ratio in 9 day old broiler chicks.

Music has been associated with the treatment of human disease since ancient times, and its many physiological and psychological effects on humans is well known. Effects of music on animals, however, has not been well studied. Popular publications report that music can be used to increase milk production in dairy cows, and recent studies indicate that swine may also respond in a favorable manner. No significant influence of music on precocial birds has been previously demonstrated. In one study, meat type chicks were exposed to different kinds of continuous music, and it was stated that low level dinner music improved body gain weight and food:gain ratio very slightly, though the data was not statistically significant.

Until now, the use of filial imprinting, environmental enrichment and music in combination to improve behavioral characteristics, feeding habits and mortality rates in precocial birds has not been suggested or attempted. It has now been found experimentally, that this triple combination has a significant effect on these parameters.

Toys are objects which can be utilized by an animal for play. Play in animals has been described as "leaping; jumping; bucking or running when there is no obstacle to overcome, no enemy to fee, or object to obtain; sniffing; licking, pawing and manipulating familiar rather than novel objects; sex without coition; and, fighting in friendly rather than aggressive encounters which avoids injuring or routing the partner." (McFarland, 1981). According to McFarland, there are at least five categories of play activities:

1. Superfluous activity includes prancing, frisking, leaping, gambolling, etc., and has been in observed cattle, horses, sheep, goats and chicks.

2. Aimless exploration, manipulation and object play involves the use of novel stimuli and objects which typically elicit approach, touching, mouthing and other manipulations, providing the animal is not frightened.

3. Practice play is often seen in animals whose movement is still not perfected at birth, and involves the repetition and elaboration of newly acquired and chance actions.

4. Responses to the wrong object are often found in young animals, and comprise innate stereotyped movements to inappropriate objects.

5. Finally, social play is play between young animals and between the young and their parents. It has been suggested that social play may serve to establish dominance relationships, or to control aggression between group members.

Toys are the objects for animal play, and serve to stimulate other kinds of play or activity. Toys were developed and have been used for many years for pets (for cats, dogs, birds and aquarium fish). Farm animals, unlike pets and wild animals, however, remain in poor and monotonic environments for the majority of their lives without any objects or toys to stimulate their senses. Since it appears that all animals require a certain amount of play type activity, it would appear to be beneficial to farm animals to enhance or enrich their playing environment. If such an enrichment to their playing environment results in improved behavioral characteristics, feeding habits and mortality rates, for example, the derived economic benefit can be substantial, especially in a commercial farm environment where large numbers of animals are involved.

SUMMARY OF THE INVENTION

It is therefore the object of the present invention to provide a method for raising precocial birds, wherein the behavioral characteristics, feeding habits, mortality rates and overall health and quality of the birds are significantly improved, and the raising process is thereby made more efficient and economical.

It is another object of the present invention to provide a method for raising farm animals including mammals, birds and fish, by providing the animals with toys for play, and thereby improving their behavioral characteristics, feeding habits, mortality rates and overall health and quality.

These and other objects of the invention are achieved in one preferred embodiment by exposing precocial birds, as they are raised, to the combined effects of filial imprinting, environmental enrichment and musical sounds. In this preferred embodiment of the invention, red or blue colored objects are utilized as filial imprinting objects, and are placed in the living area of the birds. A sound system is also provided with the objects to generate music. Environmental enrichment is attained through the use of heat near the imprinting objects, and soft textured material on the objects, both of which appear to increase the tendency of chicks to remain near the imprinting object.

Using the above method, experiments have shown significant increases in the percentage of birds feeding and the body weight of the birds, and significant decreases in the amount of food consumed to body weight gained ratio, mortality rate and fear.

In another preferred embodiment of the present invention, farm animals are exposed to different types of toys during their raising period. In a number of experiments, different types of farm animals were provided with various types of toys, and significant improvements in feeding habits, mortality rates and overall health and behavior, were observed.

DETAILED DESCRIPTION OF THE PREFERRED EMBODIMENTS OF THE INVENTION

Turning now to a more detailed consideration of the invention, controlled experiments were conducted on flocks of heavy strain chicks. One flock of chicks was subjected to filial imprinting, environmental enrichment and music, while a second flock of chicks was used as the control group, and not exposed to any of these stimuli.

The experimental group was disposed in a pen containing one or more imprinting or enrichment objects of predetermined shape or color. In the experiments, good results were obtained with one or more blue plastic cubes or boxes having sides of between about 10 cm. and 50 cm. in length. It has been established that chicks unlearned color preferences are bimodal, with peaks at short and long wavelengths. This explains the results of the experiments conducted in conjunction with the present invention, in which it was found that a large group of broiler chicks preferred to follow blue or red objects. Thus, the selected color of the imprinting object is important.

Chicks are also known to be attracted to heat and soft textured materials. Environmental enrichment was thus attained in the experiment by providing an infrared bulb, or other kind of heat radiator, proximate and preferably above the imprinting object. The temperature apparent to the chicks from the radiation source should be above the ambient temperature but obviously below a temperature that causes discomfort and harm to the chicks. Also, a soft textured material was disposed on each box to provide soft contact between the chicks and the imprinting object. In the experiment, good results were obtained with red gloves hanging from the box at a chick's eye level, although clearly, any soft textured material would probably suffice.

To provide music, a loudspeaker was located in each of the boxes that was activated simultaneously from a tape recorder. Good results were obtained with soft or soothing music, such as classical music. While the sound system can be activated continually, generally, the sound system was activated intermittently, for example for a period of between 30 minutes and 2 hours, alternating with an intermission of about the same duration.

The following table shows the results of the experiment, and presents values that are averages between all chicks, including males and females, in each group:

TABLE 1

| | % of Birds feeding | Body weight (g) | Food:Grain ratio | Mortality (%) | T.I. (sec) |
|---|---|---|---|---|---|
| control | 9.4 | 2573 | 2.00 | 5 | 165 |
| experimental | 13.6 | 2629 | 1.96 | 2.5 | 94 |

In the experiment, the percentage of birds feeding, body weight and food:gain ratio measurements were taken on the chicks at 8 weeks of age. The mortality percentage was taken at the first two weeks, and duration of tonic immobility (T.I.), which is considered to be a fear potentiated response, was taken at 6-7 weeks of age.

As can be seen from the results, the chicks exposed to the imprinting and enrichment process and music spent significantly more time near the feeders than did the chicks in the control group. The percentage of birds feeding in the experimental group was approximately 45% greater than those feeding in the control group. As a result, body weight increased (about 2% on average, though 3% for males), and the food:gain ratio decreased (about 2%). Significantly, the mortality rate was 50% lower in the experimental group than it was in the control group. Also, in several kinds of fear tests, the experimental group was found to be significantly less fearful than the control group.

While the experimental measurements were as described, the time frame for practicing the invention is not unduly critical, for example the conjoint use of the several factors can be applied, for example from near with for at least about 2 weeks, preferably about 4 weeks, more preferably 6 weeks and most preferably at least about 8 weeks.

This experiment provided for the first time, a management program for raising heavy strain chicks that incorporates filial imprinting, environmental enrichment and music. Through combination of these three effects, surprising improvements in feeding habits, mortality rates and overall behavior have been obtained.

In another preferred embodiment of the invention, numerous experiments were conducted to test the effects of exposing various types of farm animals, including birds, fish and mammals, to toys. In a first experiment, five hundred laying hens were provided with pecking toys. Aggressive pecking by laying hens and its relation to peck order and egg production is a well known issue. Researchers have attempted to reduce aggressive pecking of laying hens for many years in order to improve production. Beak trimming and polypeepers (plastic devices restricting forward vision) have been utilized for this purpose. The purpose then of pecking toys for laying hens is so chickens will peck or play more with those toys, and less with each other.

In the experiment, at five months of age, Leghorn chickens were exposed to a metal key ring with three beads and a jingle bell. The ring (one ring for every three chickens) was hung in the center of the cage and could easily be pecked by the hens. Good results were obtained with a ring three centimeters in diameter with red, blue, and green or yellow beads attached to it.

Experiments using these toys have shown a consistent increase in egg production, and a steady decrease in feed use and mortality following seven months of production as illustrated in Table 2.

TABLE 2

|  | Egg Production (% hen-day) | Fed Usage Kg/bird | Mortality % |
| --- | --- | --- | --- |
| Control | 80.95 | 23.3 | 5.0 |
| Experimental | 81.70 | 23.0 | 3.0 |

In a second commercial experiment, 2000 laying hens were provided with pecking toys. A decrease in mortality (0.5 percent vs. 1%) and increase in egg production (2969 eggs vs. 2812 eggs (sum of 4 separate arbitrary egg countings)) resulted, following two months of production. Feed usage was not measured because of technical difficulties.

In the third and fourth experiments, fish were provided with environment enrichment toys. Environmental enrichment involves the increase of the stimulatory value of the home environment by increasing its complexity. In contrast to the many mammalian studies, very little is known about the effect of environmental enrichment on fish.

After being transferred from the hatchery, 600 Atlantic Salmon fish were exposed to marbles and plastic beads. This experiment had six replications. Good results were obtained with marbles and beads one centimeter in diameter, and in various colors. Experiments using these toys for four weeks have shown a significant ($P<0.01$) decrease in mortality as illustrated in Table 3. However, body weights of experimental fish were significantly reduced ($P<0.05$) unlike feed conversion.

TABLE 3

|  | Body weight (g) | Food:gain ratio | Mortality (%) |
| --- | --- | --- | --- |
| Control | 0.46 | 1.92 | 5 |
| Experimental | 0.43 | 1.89 | 1 |

The 4 percent differences in mortality in turn created differences in density which could explain the experimental fish's body weight reduction. For that reason, in the 6 replications of the fourth experiment, 450 Rainbow Trout were exposed to the same toys; this time, however with lower density. Four week long experiments have demonstrated (Table 4) that a significant ($P<0.05$) decrease in mortality, an increase in body weight and an improvement in food:gain ratio resulted when the toys were presented in the fish jars.

TABLE 4

|  | Body weight (g) | Food:gain ratio | Mortality (%) |
| --- | --- | --- | --- |
| Control | 0.93 | 1.71 | 5.3 |
| Experimental | 0.94 | 1.61 | 1.3 |

Finally, in a fifth experiment, lambs were provided with teething toys. A lamb, when born, may show one or two temporary incisor teeth, or none at all. By the time the lamb is about two months old, it will have cut all eight temporary or milk incisors. Just like human babies, lambs will put things in their mouths and gnaw in order to relieve teething pain. It was therefore the purpose of this experiment to create teething toys for lambs.

In the experiment, four groups of lambs were exposed at one day of age to different kinds of rubber and metal toys. The toys were hung with metal chains from the ceiling of the cage and on the cage walls. Good results were obtained with wheel shaped rubber toys 10 cm. in diameter, horseshoe shaped rubber toys 10×5 cm., and metal screws 10×1 cm. Control lambs were raised under exactly the same conditions without the toys. Observations of both control and experimental lambs were made during their first three weeks of life. Experimental lambs approached, touched and chewed the teething toys often during this period. The controls chewed the metal cage bars periodically, but this chewing behavior was not as frequent as with the experimentals.

As illustrated in Table 5, experiments using these toys have demonstrated that all four experimental groups (determined by different initial body weights) gained more weight on a percentage basis than did the controls. However no differences in the morality rates were found. Also, feed usage was not recorded because of technical difficulties (lambs were fed from bottles).

TABLE 5

| Group Number | Initial Body Weight (at 6–12 hours of age) (Kg) | Number of lambs | Final Body Weight (3 weeks) (Kg) | % Gain |
| --- | --- | --- | --- | --- |
| 1. Experimental | 1.62 | (3) | 6.17 | 380.9 |
| Control | 1.71 | (3) | 6.30 | 368.4 |
| 2. Experimental | 2.16 | (4) | 7.02 | 352.0 |
| Control | 2.03 | (4) | 6.57 | 323.6 |
| 3. Experimental | 2.48 | (6) | 7.61 | 306.9 |
| Control | 2.57 | (6) | 7.70 | 299.6 |
| 4. Experimental | 2.88 | (8) | 8.24 | 286.1 |
| Control | 2.88 | (5) | 8.15 | 283.0 |

Although further experimentation needs to be conducted to better document the results, it is clear from these preliminary experiments, that exposure of farm animals, including mammals, birds and fish, to toys, can significantly improve their behavior characteristics, feeding habits, mortality rates and overall health and quality. As a result, the raising process becomes more efficient and commercially worthwhile.

Although the invention has been disclosed in terms of specific examples, it will be understood that numerous variations and modifications could be made without departing from the true spirit and scope of the inventive concept as set forth in the following claims.

I claim:

1. A method of raising precocial birds comprising exposing precocial birds to the combined effects of filial imprinting, environmental enrichment and music for improving their feeding habits and general behavior.

2. The method of claim 1, wherein precocial birds are exposed to filial imprinting by disposing at least one filial imprinting object in a pen in which the birds are raised.

3. The method of claim 1, wherein precocial birds are exposed to filial imprinting by disposing at least one cube having sides between 10 cm. and 50 cm. in length that acts as a filial imprinting object, in a pen in which the birds are raised.

4. The method of claim 1, wherein precocial birds are exposed to environmental enrichment by exposing the birds to heat.

5. The method of claim 1, wherein precocial birds are exposed to environmental enrichment by exposing the birds to soft textured materials.

6. The method of claim 1, wherein precocial birds are exposed to soothing music for a duration between 30 minutes and 2 hours, followed by an intermission of the same duration.

7. The method of claim 2, wherein the imprinting object is blue or red.

8. The method of claim 1, wherein precocial birds are exposed to soft soothing music.

9. The method of claim 1, wherein precocial birds are exposed to classical music.

* * * * *